United States Patent [19]
Wren

[11] Patent Number: 5,852,025
[45] Date of Patent: Dec. 22, 1998

[54] COMPOSITIONS AND METHODS FOR CONTROLLING PEST INSECTS

[75] Inventor: Heather N. Wren, New Castle, Va.

[73] Assignee: Virginia Tech Intellectual Properties, Inc., Blacksburg, Va.

[21] Appl. No.: 833,758

[22] Filed: Apr. 9, 1997

Related U.S. Application Data

[62] Division of Ser. No. 457,705, Jun. 1, 1995, Pat. No. 5,620,982, which is a division of Ser. No. 291,072, Aug. 17, 1994, Pat. No. 5,514,681.

[51] Int. Cl.$^6$ .......................... A01N 25/00; A01N 43/54; A01N 43/60; A01N 43/90
[52] U.S. Cl. ........................... 514/262; 424/84; 514/249; 514/263; 514/264; 514/275; 514/258
[58] Field of Search ..................................... 514/262, 258, 514/263, 264, 275, 249; 424/84

[56] References Cited

U.S. PATENT DOCUMENTS

| | | | |
|---|---|---|---|
| 4,857,532 | 8/1989 | Koehler et al. | 514/262 |
| 4,883,801 | 11/1989 | Nathanson | 514/263 |
| 4,902,690 | 2/1990 | Nathanson | 514/213 |

OTHER PUBLICATIONS

Wren, "Tem Evidence of Urocytes in the Cockroach Fat Body", *Tissue and Cell* 23(2):291–292 (1991).

Mullins et al., "Maternal and Paternal Nitrogen Investment in *Blattella Germanica* (L.) (Dictyoptera; Blattellidae)", *J. exp. Biol.* 162:55–72 (1992).

Engebretson & Mullins, "Effects of a Purine Inhibitor, Allopurinol, on Urate Metabolism in the German Cockroach, *Blattella Germanica* L. (Dictyoptera: Blattellidae)", *Comp. Biochem. Physiol.* 83B(1):93–97 (1986).

Suiter et al., "Dietary Effects of Allopurinol and Sulfinpyrazone on Development, Survival, and Reproduction of German Cockroaches (Dictyoptera: Blattellidae)", *J. Econ. Entomol.* 85(1):117–122 (1992).

Wren & Cochran, "Xanthine Dehydrogenase Activity in the Cockroach Endosymbiont *Blattabacterium Cuenoti* (Mercier 1906) Hollande and Favre 1931 and in the Cockroach Fat Body", *Comp. Biochem. Physiol.* 88B(3):1023–1026 (1987).

Cruden & Markovetz, "Microbial Ecology of the Cockroach Gut", *Ann. Rev. Microbiol.* 41:617–643 (1987).

Suiter et al., "Age– and Sex–Related Effects in German Cockroaches Fed an Allopurinol Diet (Dictyoptera: Blattellidae)", *J. Med. Entomol.* 30(5):907–912 (1993).

Cochran, "Feeding, Drinking and Urate Excretory Cycles in Reproducing Female Parcoblatta Cockroaches", *Comp. Biochem. Physiol.* 84A(4):677–682 (1986).

Wigglesworth, "Histochemical Studies of Uric Acid in Some Insects. I. Storage in the Fat Body of *Periplaneta Americana* and the Action of the Symbiotic Bacteria", *Tissue and Cell* 19(1):83–91 (1987).

Cochran, "Comparative Analysis of Excreta from Twenty Cockroach Species", *Comp. Biochem. Physiol.* 46A:409–419 (1973).

Mullins & Cochran, "Nitrogen Excretion in Cockroaches: Uric Acid is Not a Major Product", *Science* 177:699–701 (1972).

Massey et al., "On the Mechanism of Inactivation of Xanthine Oxidase by Allopurinol and Other Pyrazolo[3,4–d]pyrimidines", *J. Biol. Chem.* 245(11):2837–2844 (1970).

Slansky, "Xanthine Toxicity to Caterpillars Synergized by Allopurinol, a Xanthine Dehyrdogenase/Oxidase Inhibitor", *J. Chem. Ecol.* 19(11):2635–2560 (1993).

*Primary Examiner*—Allen J. Robinson
*Attorney, Agent, or Firm*—Pennie & Edmonds LLP

[57] ABSTRACT

Compositions of a purine, a xanthine oxidase inhibitor and/or a dihydrofolate reductase inhibitor, and methods of using same, for controlling the growth of pest insects which salvage, store, or excrete their nitrogenous wastes via the purine metabolic pathway.

30 Claims, 1 Drawing Sheet

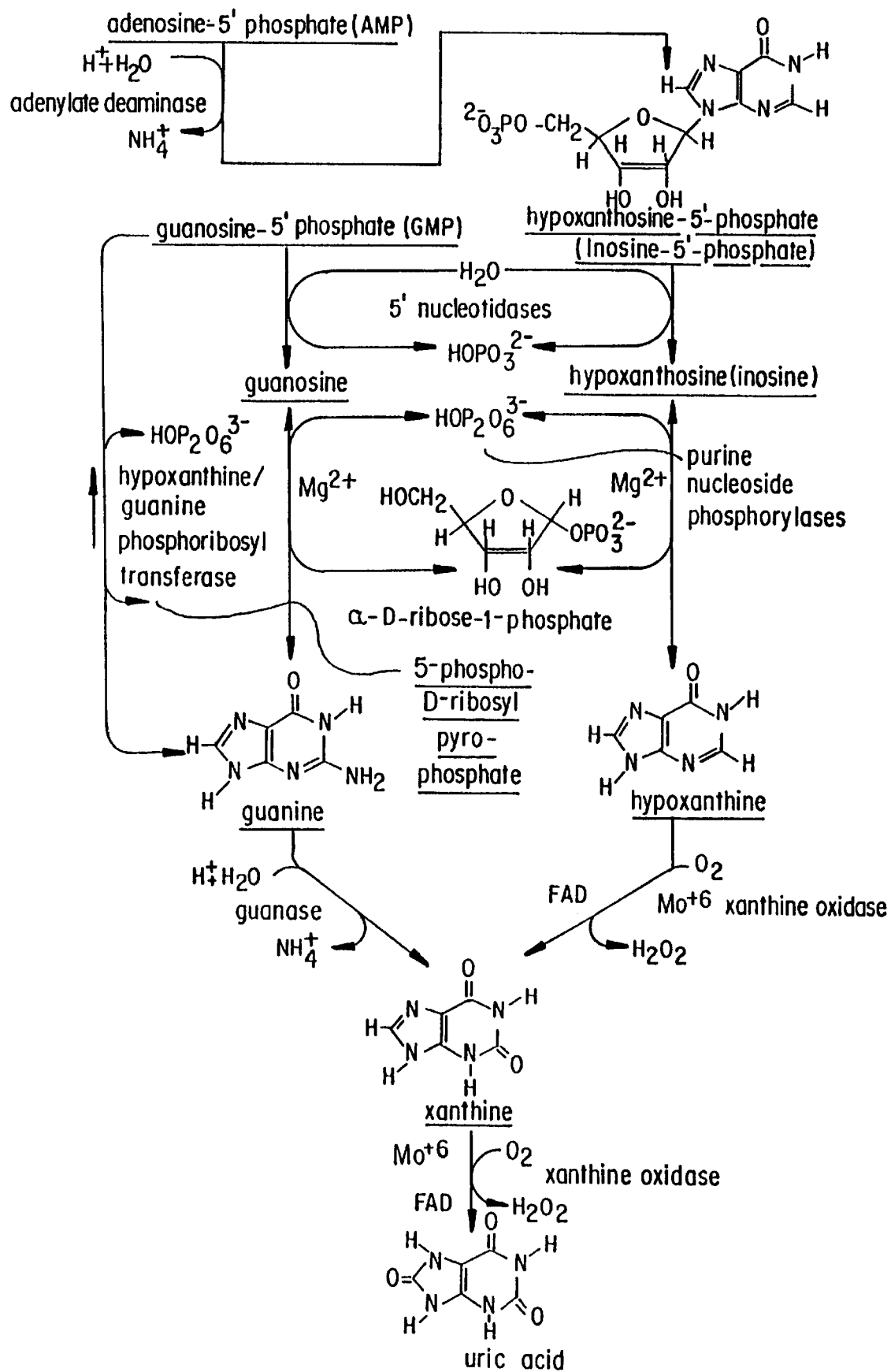

COMPOSITIONS AND METHODS FOR CONTROLLING PEST INSECTS

This is a division of application Ser. No. 08/457,705, filed Jun. 1, 1995, now U.S. Pat. No. 5,620,982, which is a division of application Ser. No. 08/291,072, filed Aug. 17, 1994, now U.S. Pat. No. 5,514,681, issued May 7, 1996.

BACKGROUND OF INVENTION

1. Field of the Invention

The present invention is directed to the regulation of the growth of pest insects which utilize the purine metabolic pathway to salvage, store, or excrete their nitrogenous wastes. It comprises bringing into contact with the pest insects, formulations containing growth-controlling amounts of compositions comprising purines, purine metabolic-enzyme inhibitors, and inhibitors of enzymes which regulate production of specific co-factors of this pathway.

2. Description of the Background Art

Despite the recent development and great promise of such advanced insect-controlling techniques as chemical sterilants, pheromones, and ecologically-based control strategies, the use of chemical insecticides still plays a predominant role. However, rising public awareness of environmental issues, more stringent government regulations, and increasing insect resistance to conventional modalities are driving the pest control industry to seek safer alternatives to these conventional chemical insecticides.

Others have attempted to identify and evaluate the efficacy of insect growth inhibitors. However, given the continuous need for increased selectivity and effectiveness of insect control agents, it became desirable to engage in rational formulation of control agents based on an understanding of key insect nutritional and metabolic pathways.

SUMMARY OF THE INVENTION

It is widely acknowledged that the majority of insects are uricotelic in that they excrete their excess nitrogen as uric acid and uricolytic derivatives thereof (Cochran (1975), "Excretion in Insects" in *Insect Biochemistry and Function* pp. 171–281). The uric acid is synthesized, via the purine catabolic pathway shown in FIG. 1, and is either excreted to the outside, or, in some cases, stored by the insect as a metabolic reserve.

Cockroaches are a good model of the essential nature of storage-excretion of uric acid. For example, in German cockroaches, a slurry of uric acid is passed to the female during mating, as a paternal investment. The female, in turn, invests the developing eggs with a supply of uric acid that is used during embryogenesis (Mullins & Keil (1980), *Nature* 283: 567–569). Interruption of this vital cycle appears highly detrimental to cockroach population growth, which depends heavily on these uric acid stores (Engebretson & Mullins (1986), *Comp. Biochem. Physiol.* 83B: 93–97; Suiter et al. (1992), *J. Econ. Entomol.* 85(1): 117–122). In the cockroach fat body, de novo synthesis of uric acid takes place, largely through purine salvage, in the trophocytes and the uric acid is stored in specialized urocytes for recycling (Cochran (1985), *Ann. Rev. Entomol.* 30: 29–49). This is accomplished through uricolytic digestion of the stored urates by endosymbiont bacteria which are sequestered in bacteriocyte cells adjacent to the urocytes (Wren & Cochran (1987), *Comp. Biochem. Physiol.* 88B: 1023–1026). In this part of the uric acid cycle, the endosymbiont bacteria use xanthine dehydrogenase to reduce the urates to xanthine, and disruption of any part of this system also inhibits population growth.

Another essential facet of insect physiology is the molt cycle, when the cuticular epithelial cells multiply and synthesize a new, larger exoskeleton just prior to ecdysis (Chapman (1982), *The Insects Structure and Function.* Cambridge, Mass.: Harvard University Press; Hepburn (1985), "The Integument" in *Fundamentals of Insect Physiology.* Ed. M. S. Blum, pp. 139–183. New York: John Wiley & Sons, Inc.). At the same time, many of the internal tissues are growing, as in cockroaches where, for example, development of the internal and external reproductive organs progresses with each stage, culminating at the final molt to the sexually mature adult (Chapman (1982) *The Insects Structure and Function,* Cambridge Mass.: Harvard University Press). During this process, insects draw heavily on their metabolic reserves to achieve the rapid growth of cells which takes place.

The purine metabolic pathway is central to all of these processes, and, thus, to homeostasis of insects. As in any of the known biochemical pathways, the hydrolytic enzymes and their co-factors are essential to the functioning of the purine degradative pathway. This pathway also serves to salvage the free purine bases for re-use in nucleotide and nucleic acid biosynthesis (Lehninger (1970) Biochemistry: The Molecular Basis of Cell Structure and Function. 2nd Ed. pp. 740–742).

Two of the enzymes involved in this pathway are xanthine oxidase and dihydrofolate reductase (also known as tetrahydrofolate dehydrogenase). Xanthine oxidase (E.C. 1.2.3.2), a molybdenum iron sulfur flavo-enzyme, functions late in the salvage pathway of purine catabolism from guanosine monophosphate and inosine monophosphate to xanthine, and finally, to uric acid. In this pathway, xanthine oxidase catalyzes both the conversion of hypoxanthine to xanthine, and the conversion of xanthine to uric acid (Coughlan (1980) *Molybdenum and Molybdenum-Containing Enzymes.* New York: Pergamon Press). Functioning as xanthine dehydrogenase, the same enzyme reduces uric acid to xanthine in the uricolytic pathway of the endosymbiont bacteria in the cockroach fat body (Wren & Cochran (1987), *Comp. Biochem. Physiol.* 88B: 1023–1026). Dihydrofolate reductase catalyzes the synthesis of tetrahydrofolate, which is an essential co-factor in the uric acid and purine synthesis pathways (Kucers & Bennett (1979), "Trimethoprim and Cotrimoxazole" in *The Use of Antibiotics.* 3rd Ed. London: William Heinemann Medical Books, Ltd.).

An understanding of these insect systems, which rely on the recycling and excretion of their purines, led to the present invention, which provides novel compositions and methods for disrupting insect homeostasis and inhibiting insect population growth. Thus, in one embodiment, these compositions comprise (1) a purine such as guanine (2-amino-1,7-dihydro-6H-purin-6-one); hypoxanthine (1,7-dihydro-6H-purin-6-one); or xanthine (3,7-dihydro-1H-purine-2,6-dione), and mixtures thereof, and (2) a xanthine oxidase inhibitor, preferably one of the 6-unsubstituted pyrazolo[3,4-d]pyrimidine group, such as oxypurinol (4,6-dihydroxypyrazolo [3,4-d]pyrimidine); 4-mercapto-6-hydroxypyrazolo[3,4-d]pyrimidine; 4,6-dimercaptopyrazolo[3,4-d]pyrimidine, 4-amino-6-hydroxypyrazolo[3,4-d]pyrimidine; 4-hydroxy-6-mercapto [3,4-d]pyrimidine; or allopurinol (4-hydroxypyrazolo[3,4-d] pyrimidine), and mixtures thereof. In another embodiment, these compositions comprise (1) a purine; (2) a xanthine oxidase inhibitor; and (3) a dihydrofolate reductase inhibitor such as trimethoprim (2,4-diamino-5-(3,4,5-trimethoxybenzyl)-pyrimidine), methotrexate (N-[4-[[(2,4-diamino-6-pteridinyl)methyl]methylamino]benzoyl]-L-glutamic acid), or pyrimethamine (5-(4-chlorophenyl)-6-ethyl-2,4-pyrimidinediamine), and mixtures thereof.

While specific purines in combination with specific enzyme inhibitors are utilized to illustrate the present invention, it is understood that any of the purines and inhibitors of any of the enzymes of the pathway of FIG. 1 may be applied according to the present invention.

Furthermore, while the cockroach is utilized to illustrate the present invention, it is understood that the compositions and methods of the present invention may be applied to regulate the growth of any pest insect which utilizes the purine metabolic pathway to salvage, store, or excrete to the outside, its nitrogen wastes.

A further embodiment of the invention comprises an insect bait or attractant formulation containing an insect-growth-regulating effective amount of the compositions.

DESCRIPTION OF THE FIGURES

FIG. 1 shows the pathway for purine catabolism.

DETAILED DESCRIPTION OF THE INVENTION

The present invention is predicated on the discovery that ingestion of formulations containing growth controlling amounts of certain novel compositions by pest insects, particularly cockroaches, disrupts homeostasis and inhibits population growth.

The compositions of the present invention may be the sole active ingredients of the formulation or they may be admixed with one or more additional active ingredients, such as other, conventional insecticides.

The compositions of the present invention may be formulated with a "bait" or "attractant." For purposes of description of the present invention, these terms refer to any formulation to which pest insects are attracted and which they will ingest. Such compositions are well-known to those skilled in the art and it will be understood that any such material which is inert with respect to the compositions of the present invention may be employed in the practice of the invention.

In use, the formulations may be applied to the pest insects, to the locus of the pest insects, and/or to the habitat of the pest insects.

The following examples are included for purposes of illustration only and are not intended to be limiting, unless otherwise specified.

EXAMPLE 1

General Procedure

German cockroaches (*Blatella germanica* L.) from the stock laboratory "VPI" strain were used to form experimental colonies of mixed life stages. Unless otherwise specified, each insect colony of 42 insects contained five each of newly post-emergent adult males and females, eight each of male and female nymphs at the fifth nymphal stage, and eight each of male and female nymphs at the third nymphal stage. Care was taken to select insects from the same stock colonies for each experimental block, and each colony was allowed to acclimatize for twenty-four (24) hours prior to treatment.

The colonies were housed in one-gallon glass battery jars fitted with fiber-board platforms, with clean tap-water offered continuously in cotton-stoppered glass vials. The jars were rimmed with a thin coating of petrolatum, and covered closely with three layers of cheesecloth held in place with strong elastic bands. These measures prevented escape of the test insects, as well as contamination by other insects.

Each test included "control" colonies, in which the food was untreated, and "test" colonies, in which the food was mixed with the compositions being tested to form percent concentrations by weight (w/w). Unless otherwise specified, the food was Agway Laboratory Rat Chow and was prepared by grinding the chow pellets to a fine powder and, for test colonies, incorporating the test compounds by grinding and mixing them with the chow, using a mortar and pestle. Food, either treated or untreated, was pre-weighed in stainless steel planchettes and offered with the planchettes placed in plastic cups, to avoid loss through spillage. During tests, the planchettes were weighed weekly and food replenished when necessary.

Replicate colonies were initiated on consecutive days, with all colonies housed in the stock laboratory under the same conditions of ambient temperature (25° C.), and humidity as during rearing. A control "blank colony", which was identical to a control colony except that no insects were included, was monitored for loss or gain of moisture in the food due to changes in ambient humidity. Any such changes were factored into the calculations of food consumption.

A record was kept of all dead insects, which were counted and sexed weekly when the food was weighed. Dead insects were frozen and stored at −4° C. prior to being subjected to a whole-body uric acid assay. Unless otherwise specified, the total population of each colony was counted every three (3) weeks. When all of the insects, or all of the females, were dead or moribund, the colony was determined to be non-viable and the experiment was terminated. Remaining insects were killed by freezing and stored frozen, as above, to await assaying for uric acid.

The mean percent change ($\Delta\%$) in population number for each colony was calculated, with the initial number (42) representing 100%. Food consumption, in milligrams per individual cockroach (ICmg), was calculated for the first three (3) weeks of the experiment, prior to nymphs hatching. These measurements determined whether the test compositions were ingested, and whether such compositions were effective in inhibiting population growth.

EXAMPLE 2

Uric Acid Assay

Determination of the whole-body uric acid content of the dead cockroaches was conducted essentially according to a standard uricase assay (Cochran (1973) *Comp. Biochem. Physiol.* A46: 409–419). Individual cockroaches, with wings and legs trimmed off, were dried for 24–48 hours at 60° C., weighed, and ground to a fine powder. Uric acid was extracted from the dry tissue with 0.6% aqueous lithium carbonate for three (3) hours at 60° C. with continuous shaking. The extracts were centrifuged to remove tissue debris. After mixing with uricase, the maximum absorption at 292 nm was determined spectrophotometrically, and uric acid concentration was calculated in $\mu$g uric acid/mg of dry tissue.

EXAMPLE 3

Assessment of Xanthine Food Compositions

In two experiments (3a) and (3b), the effects of adding 1% xanthine [Sigma Chemical Co.] to the basic cockroach diet of ground rat chow, were studied. The colonies in each experiment were set up as described in Example I, with the diets being either rat chow alone (RC), or rat chow+1% xanthine (RCX). Each experiment included three replicate colonies for each condition (n=3).

The populations were counted at 6 and 9 weeks (3a) or 10 and 12 weeks (3b), and the percent change in mean population numbers ($\Delta\%$) was calculated. Individual consumption (ICmg) of the diets for the first three weeks of treatment was calculated from the food-weight data.

The results are shown in Table 1. The addition of xanthine appeared neither to inhibit feeding nor to adversely affect population growth. In fact, xanthine appeared to enhance reproduction, as population numbers were higher in xanthine-treated colonies than in those fed rat chow alone.

The percent change ($\Delta\%$) in mean colony population numbers at 5.5, 6, 7, 9, 10 and 12 weeks of treatment were determined as described, with the results shown in Table 2b below. The addition of oxypurinol alone to the diet did not inhibit population growth. The addition of xanthine plus oxypurinol inhibited population growth to the point of extinction.

TABLE 1

| TIME | EXPERIMENT 3a | | | | EXPERIMENT 3b | | | |
|---|---|---|---|---|---|---|---|---|
| | ICmg ($\pm$SEM) | | $\Delta\%$(*) | | ICmg ($\pm$SEM) | | $\Delta\%$ | |
| (wk) | RC | RCX | RC | RCX | RC | RCX | RC | RCX |
| 3 | 55.8 ($\pm$0.9) | 55.3 ($\pm$2.7) | | | 58.0 ($\pm$0.4) | 57.9 ($\pm$0.8) | | |
| 6 | | | +224% | +278% | | | | |
| 9 | | | +707% | +921% | | | | |
| 10 | | | | | | | +1405% | +1433% |
| 12 | | | | | | | +1774% | +1869% |

(*) + = increase
Table 1: Mean individual consumption (ICmg) and percent change ($\Delta\%$) in mean population number over time (weeks), in colonies of German cockroaches administered offered food without (RC) or with 1% xanthine (RCX). n = 3

EXAMPLE 4

Assessment of Xanthine-Oxypurinol Compositions

Colonies of German cockroaches were prepared as described. The diets administered were rat chow alone (RC); rat chow with oxypurinol [Sigma Chemical Co.] (RC+OXY%); and rat chow with 1% xanthine (RCX) and with oxypurinol (+OXY%) at five concentrations (w/w). Individual consumption (ICmg), population growth control, and whole-body uric acid concentrations were determined.

Individual consumption (ICmg) in the first three weeks was calculated, and the results shown in Table 2a below. The addition of oxypurinol alone caused a decrease in food consumption over controls fed untreated food. The addition of xanthine to the diet caused the consumption of oxypurinol-treated food to increase by 35% at 0.1% oxypurinol concentration, and by 56% at the 1.0% oxypurinol concentration.

TABLE 2a

| | XANTHINE 0% | | | XANTHINE 1% | | | | |
|---|---|---|---|---|---|---|---|---|
| TIME | | RC + OXY % | | RC + OXY % | | | | |
| (wk) | RC | 0.1 | 1.0 | 0.1 | 0.5 | 1.0 | 2.0 | 3.0 |
| 3 | 53.7 (*2.0) n = 9* | 36 n = 1 | 32 n = 1 | 48.5 (*1.4) n = 6 | 58.3 (*0.8) n = 3 | 49.9 (*1.9) n = 6 | 52.6 (*1.5) n = 6 | 45.6 n = 1 |

* = number of colonies
Table 2a: Mean individual consumption (ICmg) of rat chow over three weeks, with or without 1% xanthine, and with various concentrations (w/w) of oxypurinol (OXY %).

TABLE 2b

| TIME | XANTHINE 0% | | | XANTHINE 1% | | | | |
|---|---|---|---|---|---|---|---|---|
| | RC | RC + OXY % | | RC + OXY % | | | | |
| (wks) | CONTROL | 0.1 | 1.0 | 0.1 | 0.5 | 1.0 | 2.0 | 3.0 |
| 5.5 | +690% n = 1 | +460% n = 1 | +1060% n = 1 | | | | | |
| 6 | +126% n = 5 | | | −31% | −50% | −5% | −11% | −55% |
| 9 | +812% n = 5 | | | −92% | −92% | −64% | −77% | −88% |
| 7 | +719% | | | −64% | | −75% | −69% | |
| 10 | +1405% | | | −91% | | −98% | −98% | |
| 12 | +1774% | | | −94% | | −100% | −100% | |

Table 2b: Percent changes (+ or − Δ%) in mean population number, in colonies of German cockroaches offered food with or without 1% xanthine, and with various concentrations (w/w) of oxypurinol (OXY %), over time (weeks). Except where noted, n = 3.

Whole-body uric acid concentrations were calculated from standard uricase assays for cockroaches that died during weeks 5–9 of treatment. Samples from the VPI laboratory strain of German cockroaches also were assayed to show typical "base-line" levels of urates before treatment.

As shown in Table 2c below, females in the VPI strain typically exhibit a slightly higher uric acid level than males, regardless of stage. However, as shown in Tables 2d–2f below, after several weeks of feeding with xanthine and oxypurinol in the diet, there is a marked decline in whole-body urate concentration in all groups regardless of age or sex.

TABLE 2c

| STAGE | GENDER | AGE (wks) | URIC ACID $\mu$g/mg ± SEM |
|---|---|---|---|
| adult | males n = 9 | 6–7 | 1.80 ±0.12 |
| | females n = 10 | | 2.41 ±0.06 |
| nymph | males n = 10 | 5–6 | 2.34 ±0.10 |
| | females n = 10 | | 2.44 ±0.22 |
| nymph | males n = 10 | 3–4 | 0.77 ±0.10 |
| | females n = 10 | | 1.51 ±0.10p |

Table 2c: Mean, whole-body uric acid concentrations ($\mu$g/mg of dry tissue weight, ±SEM), in different age and gender groups of the VPI laboratory strain of German cockroaches that are typical of those used in the feeding experiments.

TABLE 2d

| TIME | | RCX + OXY % | | |
|---|---|---|---|---|
| (wks) | RC | 0.1 | 1.0 | 2.0 |
| 5 | 2.42 ±0.12 n = 5 | 0.54 ±0.05 n = 25 | 0.32 ±0.06 n = 17 | 0.31 ±0.05 n = 17 |
| 6 | 2.79 ±0.21 n = 4 | 0.43 ±0.04 n = 32 | 0.30 ±0.04 n = 35 | 0.27 ±0.03 n = 26 |
| 7 | 2.78 ±0.25 n = 6 | 0.54 ±0.10 n = 8 | 0.25 ±0.04 n = 14 | 0.21 ±0.04 n = 12 |
| 9 | 3.16 ±0.06 n = 10 | 0.51 n = 1 | 0.14 ±0.04 n = 7 | 0.32 ±0.10 n = 3 |

TABLE 2d: Mean whole-body uric acid concentrations ($\mu$g/mg dry tissue weight ±SEM) in male German cockroaches on food without (RC), or with 1% xanthine (RCX) and various percent concentrations (w/w) of oxypurinol (OXY %).

TABLE 2e

| TIME | | RCX + OXY % | | |
|---|---|---|---|---|
| (wks) | RC | 0.1 | 1.0 | 2.0 |
| 5 | 2.63 ±0.14 n = 3 | 0.31 ±0.13 n = 6 | 0.31 ±0.04 n = 8 | 0.28 ±0.08 n = 7 |
| 6 | 3.13 ±0.04 n = 4 | 0.31 ±0.03 n = 27 | 0.34 ±0.06 n = 27 | 0.35 ±0.06 n = 18 |
| 7 | 2.95 ±0.18 n = 4 | 0.43 ±0.04 n = 24 | 0.22 ±0.04 n = 23 | 0.26 ±0.06 n = 14 |
| 9 | 3.14 n = 1 | 0.21 ±0.03 n = 21 | 0.29 ±0.04 n = 14 | 0.34 ±0.05 n = 13 |

Table 2e: Mean whole-body uric acid concentrations ($\mu$g/mg dry tissue weight ±SEM) in female German cockroaches on food without (RC) or with 1% xanthine (RCX) and various percent concentrations (w/w) of oxypurinol (OXY).

TABLE 2f

| TIME | | RCX + OXY % | | |
|---|---|---|---|---|
| (wks) | RC | 0.1 | 1.0 | 2.0 |
| 5 | 1.95 ±0.36 n = 4 | 0.53 ±0.04 n = 3 | 0.32 ±0.18 n = 2 | |
| 6 | 2.95 ±0.09 n = 5 | | | 0.08 ±0.06 n = 2 |
| 7 | 3.14 ±0.03 n = 4 | | | 0.13 ±0.08 n = 2 |

TABLE 2f-continued

| TIME | | RCX + OXY % | |
|---|---|---|---|
| (wks) | RC | 0.1 | 1.0 | 2.0 |
| 9 | 3.26<br>n = 1 | | | 0.14<br>n = 1 |

Table 2f: Mean whole-body uric acid concentrations ($\mu$g/mg dry tissue weight ±SEM) in German cockroach nymphs offered food without (RC), or with 1% xanthine (RCX) and various percent concentrations (w/w) of oxypurinol (OXY).

EXAMPLE 5

Assessment of Xanthine-Oxypurinol Compositions Offered for Different Durations

Colonies were prepared as described. The food was treated with 1% xanthine and various concentrations of oxypurinol, and was offered for durations of either 24 hours, or 1, 2, or 3 weeks. At the end of the treatment time, the treated food was removed, and the insects were offered untreated rat chow for the remainder of the test time.

As shown in Table 3 below, the data indicates that a minimum dose of oxypurinol must be ingested over time to achieve population inhibition. For example, the 24-hour treatment affected population numbers when compared with the control, but did not control population numbers at any concentration of oxypurinol. Calculation revealed that the individual consumption of oxypurinol ingested during this time ranged from 6–104 $\mu$g.

TABLE 3

Percent change (+ or –) in mean population numbers in colonies fed a diet of rat chow alone (RC), or rat chow combined with 1% xanthine (RCX), and with various concentrations. (w/w) of oxypurinol (OXY %). Duration of treatments was 24 hrs, or 1, 2, or 3 weeks, after which rat chow alone was offered. n = 3.

| TREATMENT<br>DURATION | TIME<br>(wks) | RC | RCX + OXY % | | |
|---|---|---|---|---|---|
| | | | 0.1 | 1.0 | 2.0 |
| 2.4 hours | 6 | +500% | +250% | +114% | +109% |
| 1 week | 6 | +887% | +137% | –45% | –49% |
| | 9 | +1157% | +320% | –63% | –57% |
| | 12 | +1560% | +853% | –5% | –31% |
| 2 weeks | 9 | +591% | +36% | –65% | –90% |
| | 12 | +750% | +213% | –66% | –94% |
| | 15 | >+750% | +561% | –45% | –96% |
| 3 weeks | 6 | +391% | –58% | –71% | –92% |
| | 9 | +1050% | –71% | –92% | –97% |
| | 12 | +1604% | –79% | –96% | –98% |

Treatment with 0.1% oxypurinol for one or two weeks also resulted in lower population numbers when compared with controls, and delayed egg-hatch by 1–2 weeks, but the treated colonies were recovering when they were terminated at 12 weeks. However, three (3) weeks of treatment at 0.1% oxypurinol did cause a substantial reduction in population numbers in the weeks following treatment, with no recovery noted by 12 weeks, and with only one viable eggcase, which hatched six weeks later than normal.

Colonies treated for two (2) weeks with 2% oxypurinol, or for three (3) weeks with 1% or 2% oxypurinol did not recover, even when the "recovery" time was extended to fifteen (15) weeks. Mean individual consumption of oxypurinol was 734 $\mu$g, 579 $\mu$g, and 1,140 $\mu$g respectively.

EXAMPLE 6

Assessment of Food Choice

Colonies were prepared as described, with three replicates of each condition. Planchettes containing either untreated food (RC) or food treated with xanthine+oxypurinol (RCX+ 0%) were offered together in each colony. Food weights for each planchette were calculated to determine how much of each was consumed. The treatments consisted of rat chow with 1% xanthine and oxypurinol at either 0.1%, 0.5% or 1.0% (w/w) concentration. The control colony was given two planchettes of untreated rat chow.

The results, as shown in Table 4 below, indicate that the insects consumed either the same quantity of treated and untreated food (at 0.5% oxypurinol), or ate more of the treated than the untreated food (at 0.1% and 2.0% oxypurinol). The range of oxypurinol ingested was calculated to be between 29 $\mu$g and 265 $\mu$g per individual over the first three weeks, and a high level of population-growth control was achieved, especially at 1.0% oxypurinol concentration.

TABLE 4

Individual consumption (ICmg) and percent change in
mean population numbers (Δ%) over time (wks), in colonies where
treated (RCX ± 0%) and untreated (RC) food were offered together
as a choice of diet. The amount of oxypurinol ingested over
the first three weeks is shown as μg/individual (IC μg OXY), and
the ratio of treated and untreated food consumed is given as a
percent of the total amount eaten (% TOTAL).

| TIME (wks) | TEST | RC CONTROL | RC | RCX + 0% 0.1 | RC | RCX + 0% 0.5 | RC | RCX + 0% 1.0 |
|---|---|---|---|---|---|---|---|---|
| 3 | ICmg | 58.9 | 23.1 | 29.4 | 25.7 | 25.6 | 24.7 | 26.5 |
|   | ±SEM | ±1.7 | ±3.1 | ±0.3 | ±1.O | ±1.3 | ±0.9 | ±2.O |
|   | IC μg OXY | 0 | 0 | 29.4 | 0 | 128 | 0 | 265 |
|   | % TOTAL | 100% | 43% | 57% | 50% | 50% | 48% | 52% |
| 7 | Δ% | +422% | −64% | −72% | | | | |
| 9 | Δ% | +1378% | −71% | −80% | −94% | | | |
| 12 | Δ% | +2007% | −76% | −71% | −96% | | | |

EXAMPLE 7

Life Stage Effects of Xanthine-Oxypurinol Compositions

Colonies of German cockroaches were housed as previously described, with the usually mixed stages separated into three different colonies. Colonies consisted of either newly-molted adults (five males and five females, 6–7 weeks old); large nymphs (eight males and eight females, 5–6 weeks old); or small nymphs (eight males and eight females, 3–4 eeks old). Colonies of older adults (five males and five females, 7–8 weeks old) also were tested.

Colonies were fed untreated rat chow (RC), or rat chow treated with 1% xanthine (RCX) plus various levels (w/w) of oxypurinol (OXY%). Individual consumption (ICmg) and percent change in mean population number (Δ%) were determined for each stage, and are shown in Tables 5a through 5d below, for adults, large nymphs, small nymphs, and older adults, respectively.

The data in these tables confirm that the primary impact of treatment with xanthine plus oxypurinol occurs as the cockroaches attempt to reproduce. The effect is probably caused by depletion of the insects' metabolic reserves, including uric acid stores which cannot be replaced because of irreversible enzyme inhibition. However, very small nymphs gowhich hatch in a dying colony also are affected in that they are usually too weak to survive, and rarely reach their second instar. It is probable that they are not invested with the metabolic reserves that are normally passed to them prenatally. Their continued feeding on treated food also prevents the young nymphs from developing their own metabolic stores, especially stores of uric acid.

Adult males were observed to be the first to die. At mating, adult males utilize a large part of their reserves to pass urates as well as mature sperm to the females. Females who have just produced an egg-case, which necessitates a large investment of nutritional reserves, die shortly thereafter, usually with the non-viable egg-case protruding from the ovipositor.

Cochran observed that cyclic feeding occurs in adult females in relation to egg production (Cochran (1983) *Entomol. Exp. Appl.* 34: 51–57). In this oothecal cycle, the females feed vigorously while maturing the oocytes, and sparingly while carrying an egg-case. These phenomena would account for the high feeding rates and early mortality of the newly-emerged adults (Table 5a), as well as the low feeding rates of the older adults (Table 5d). These latter females were likely to already have matured the eggs that would fill oothecae soon after the colony was assembled, and thus were in the low feeding-rate part of their cycle. Their first nymphal hatch would account for the precipitous rise in population numbers in these colonies (Table 5d), followed by the gradual weakening of the colonies as the adults attempted to reproduce further and the newly-hatched nymphs died.

Nymphs followed the same pattern of mortality as the adults, and were most affected by the treated diet after molting to the adult stage, when they normally feed vigorously in preparation for maturing their first oocytes. The delay in the rate at which the population declined in the large nymph colony (Table 5b), and small nymph colony (Table 5c), is further evidence that the major impact occurs during reproduction. This would have happened between weeks 9–11 of the experiment for these age-groups.

The effective dosage range for oxypurinol with xanthine is very wide in these experiments, causing high mortality at 99.5 μg/individual measured over three weeks in the newly-molted adults (Table 5a), and slower control at higher individual consumption rates when the colonies were started as nymphs. However, it is clear that, although there is a different effect on the cockroaches depending on their age when treatment is started, they are all affected as they attempt to reproduce.

TABLE 5a

Individual consumption (ICmg) and percent change in
mean population number (Δ%) in colonies of newly-molted adult
German cockroaches fed untreated rat chow (RC) or rat chow
treated with 1% xanthine (RCX) and various Concentrations (w/w)
of oxypurinol (OXY %).
COLONY STARTED AS ADULTS (n = 1)

| TIME | | | RCX + OXY % | | |
|---|---|---|---|---|---|
| wks | TEST | RC | 0.1 | 1.0 | 2.0 |
| 3 | ICmg | 87.0 | 99.5 | 76.8 | 84.8 |
| 3 | IC μg OXY | 0 | 99.5 | 768 | 1696 |
| 6 | Δ% | +1430% | −94% | −75% | −88% |
| 9 | Δ% | +1310% | −100% | −90% | −100% |
| 12 | Δ% | +1810% | −100% | −100% | −100% |

TABLE 5b

Individual consumption (ICmg) and percent change in mean population number (66 %) in colonies of large German cockroach nymphs (5–6 weeks old at the starting date) fed untreated rat chow (RC) or rat chow treated with 1% xanthine (RCX) and various concentrations (w/w) of oxypurinol (OXY %).
COLONY STARTED AS LARGE NYMPHS (n = 1)

| TIME wks | TEST | RC | RCX + OXY % 0.1 | 1.0 | 2.0 |
|---|---|---|---|---|---|
| 3 | ICmg | 82.8 | 76.9 | 65.3 | 79.3 |
| 3 | IC μg OXY | 0 | 76.9 | 653 | 1586 |
| 6 | Δ% | −6% | −50% | −31% | −6% |
| 9 | Δ% | +1613% | −69% | −81% | −63% |
| 12 | Δ% | +1800% | −88% | −100% | −100% |

TABLE 5c

Individual consumption (ICmg) and percent change in mean population number (Δ%) of small German cockroach nymphs (3–4 weeks old at the starting date) fed untreated rat chow (RC) or rat chow treated with 1% xanthine (RCX) and various concentrations (w/w) of oxypurinol (OXY %).
COLONY STARTED AS SMALL RYMPHS (n = 1)

| TIME wks | TEST | RC | RCX + OXY % 0.1 | 1.0 | 2.0 |
|---|---|---|---|---|---|
| 3 | ICmg | 54.9 | 53.9 | 52.4 | 40.4 |
| 3 | Ic μg OXY | 0 | 53.9 | 524 | 808 |
| 6 | Δ% | −50% | −31% | −19% | −81% |
| 9 | Δ% | +719% | −69% | −81% | −88% |
| 12 | Δ% | +775% | −88% | −100%11 | −100% |

TABLE 5d

Mean individual consumption (ICmg) and percent change in mean population number (Δ%) in colonies of older German cockroach adults (8–9 weeks old at the starting date) fed untreated rat chow (RC) or rat chow treated with 1% xanthine (RCX) and various concentrations (w/w) of oxypurinol (OXY%).
COLONY STARTED AS OLDER ADULTS (n = 3)

| TIME wks | TEST | RC | RCX + OXY % 0.1 | 1.0 | 2.0 |
|---|---|---|---|---|---|
| 3 | ICmg | 38.7 | 37.2 | 35.0 | 35.2 |
|  | ±SEM |  | ±1.9 | ±0.6 | ±1.8 |
| 3 | ICpg OXY | 0 | 37.2 | 350 | 704 |
| 6 | Δ% | +1150% | +557% | +403% | +823% |
| 9 | Δ% | +1030% | +33% | +40% | +197% |
| 12 | Δ% | +1820% | −73% | −67% | −30% |

EXAMPLE 8

Assessment of Compositions Containing Trimethoprim

Replicate colonies of German cockroaches were prepared as described. The diets administered were either rat chow alone (RC); rat chow with various concentrations of trimethoprim (RC+T%) (w/w), or rat chow with 1% xanthine (RCX) and various concentrations (w/w) of trimethoprim (T%).

As shown in Table 6a below, the addition of trimethoprim alone did not inhibit population growth, although there was some eventual weakening of the treated colonies. As shown in Table 6b below, however, the combination of xanthine and trimethoprim caused rapid inhibition of population growth.

Whole-body uric acid concentrations were calculated from standard uricase assays, as previously described. As shown in Table 6c below, uric acid metabolism was not affected by treatment with a combination of xanthine and trimethoprim.

During the first three-weeks, there was a mean Δ% of −82% of the populations in the treated colonies, with 65% of these still nymphs when they died. This represents 72% of the nymphs used for the experiment, and confirms that effects are most pronounced during nymphal molt.

TABLE 6a

Mean individual consumption (ICmg) of rat chow without (RC) or with various concentrations (w/w) of trimethoprim (RC + T%), qver time (weeks), shown in conjunction with percent change in mean population number (Δ%), in colonies of German cockroaches where the starting number (42) = 100%.
n = 5

| TIME WKS | TEST | RC | RC + T% 0.5 | 1.0 | 2.0 |
|---|---|---|---|---|---|
| 3 | ICmg | 62 | 61 | 58 | 54 |
|  | ±SEM | ±2.2 | ±3.5 | ±3.4 | ±1.7 |
| 12 | Δ% | +1398% | +1246% | +1013% | +384% |

TABLE 6b

Mean individual consumption (ICmg), and percent change in mean population number (Δ%), over time (weeks), in colonies of German cockroaches offered food without (RC), or with (RCX) 1% zanthine and various concentrations (w/w) of trimethoprim (T %), where the colony starting number (42) = 100%.

| TIME wks | TEST | RC n = 6 | RCX + T % 1.0 n = 3 | 2.0 n = 12 | 3.0 n = 3 |
|---|---|---|---|---|---|
| 1 | ICmg | 17.3 | 12.0 | 8.8 | 5.8 |
|  | ±SEM | ±2.4 | ±0.9 | ±0.7 | ±0.1 |
|  | Δ% | −1% | −4% | −28% | −41% |
| 3 | ICmg | 44.7 | 33.9 | 22.6 | 13.4 |
|  | ±SEM | ±2.1 | ±1.1 | ±2.8 | ±1.3 |
| 6 | Δ% | −16% | −23% | −77% | −98% |
|  |  | +36% | −44% | −67% | −98% |

TABLE 6c

Mean whole-body uric acid concentrations (μg/mg dry tissue weight ±SEM), in three groups of German cockroaches offered untreated food (RC), or food treated with 1% xanthine (RCX) and 2% trimethoprim (w/w).

| WEEK | GROUP | RC | RCX + 2% T |
|---|---|---|---|
| 3–4 | males | 2.04 | 2.61 |
|  |  | ±0.12 | ±0.05 |
|  |  | n = 19 | n = 9 |
|  | females | 2.54 | 2.64 |
|  |  | ±0.06 | ±0.03 |
|  |  | n = 17 | n = 3 |
|  | nymphs | 2.76 | 2.62 |
|  |  |  | ±0.12 |
|  |  | n = 1 | n = 9 |

EXAMPLE 9

Treatment of Resistant Cockroaches with Xanthine-Oxypurinol Compositions

Colonies of cockroaches were prepared as previously described, except that the insects were taken from laboratory stocks of two German cockroach strains that are known to be resistant to insecticides commonly used for cockroach control. The two strains were: (A) the Hawthorne strain, and (B) the Las Palms strain. Profiles of the resistance ratios exhibited by these two strains are shown in Table 7a below.

TABLE 7a

Resistance ratio (RR) profiles for the Hawthorne and Las Palms resistant strains, where, on a continuum of rising resistance, RR >2.0 indicates that resistance is developing, and RR ≧3.0 indicates that the gene frequency for resistance has increased. RR is calculated as (Test strain $LT_{50}$) ÷ (Susceptible strain $LT_{50}$), where $LT_{50}$ is the time it takes for the intoxicant to achieve 50% mortality in a treated population

| INSECTICIDE | HAWTHORNE | LAS PALMS |
|---|---|---|
| ORGANOPHOSPHATES | RR | |
| Diazinon | 2.0 | >75 |
| Chloropyrifos | 10.8 | >50 |
| Acephate | 2.0 | 1.2 |
| Malathion | 5.5 | >50 |
| CARBAMATES | | |
| Propoxur | 1.7 | >60 |
| Bendiocarb | 2.2 | >70 |
| PYRETHROIDS | | |
| Pyrethrins | >140 | >140 |
| Allethrin | >140 | >140 |
| Permethrin | 0.5 | 3.2 |
| Phenothrin | 0.6 | >120 |
| Fenvalerate | 0.9 | >60 |
| Esfenvalerate | 0.8 | 7.0 |
| Cyfluthrin | 1.8 | 2.5 |
| Cypermethrin | 1.6 | >80 |
| BIO-CHEMICAL | | |
| Avermectin | 2.4 | 1.5 |

Individual consumption (ICmg) in the first three-weeks was calculated as previously described. As shown in Tables 7b and 7c below, ICmg for both strains was consistent across all concentrations of the food mixtures. The Hawthorne strain exhibited a maximum decrease in consumption of 22% for a diet containing 3% oxypurinol. This represents a dose of 1,260 μg of oxypurinol over the first three weeks.

TABLE 7b

Mean individual consumption (ICmg), over time (wks) of rodent chow offered without (RC), or with 1% xanthine (RCX), and with various concentrations (w/w) of oxypurinol (OXY %), by German cockroaches of the Hawthorne and Las Palms resistant strains.

| TIME | | | RCX + OXY % | | |
|---|---|---|---|---|---|
| (wks) | RC | 0.1 | 1.0 | 2.0 | 3.0 |
| HAWTHORNE STRAIN | | | | | |
| 3 | 53.6 | 47.1 | 48.0 | 47.1 | 42.0 |
| | (±3.5) | (±0.6) | (±1.3) | (±0.5) | (±0.4) |
| | n = 4 | n = 3 | n = 3 | n = 3 | n = 4 |
| LAS PALMS STRAIN | | | | | |
| 3 | 45.2 | 39.5 | 40.0 | 40.0 | 40.3 |
| | (±1.3) | (±1.0) | (±0.4) | (±2.3) | (±0.5) |
| | n = 4. | n = 3. | n = 3 | n = 3 | n = 4 |

The effect of xanthine-oxypurinol combinations on population growth was determined as previously described. As shown in Tables 7c and 7d below, the combination controlled the population growth of both resistant strains.

TABLE 7c

Percent changes (+ or −) in mean population number in colonies of German cockroaches of the Hawthorne resistant strain, offered food without (RC) or with 1% xanthine (RCX), and with various concentrations (w/w) of oxypurinol (OXY %), over time (weeks). n = 3.

| TIME | | | RCX + OXY % | | |
|---|---|---|---|---|---|
| wks | RC | 0.1 | 1.0 | 2.0 | 3.0 |
| 6 | +438% | −32% | −22% | +12% | −21% |
| 9 | +997% | −55% | −59% | −38% | −67% |
| 12 | +1,601% | −77% | −78% | −76% | |

TABLE 7d

Percent changes (+ or −) in mean population number in colonies of German cockroaches of the Las Palms resistant strain, offered food without (RC) or with 1% xanthine (RCX), and with various concentrations (w/w) of oxypurinol, over time (weeks). n = 3.

| TIME | | | RCX + OXY % | | |
|---|---|---|---|---|---|
| wks | RC | 0.1 | 1.0 | 2.0 | 3.0 |
| 6 | +146% | +50% | +68% | +31% | −25% |
| 9 | +1,074% | −50% | −8% | −60% | −70% |
| 12 | +1,624% | −78% | −67% | −88% | −95% |

EXAMPLE 10

Treatment of Resistant Cockroaches with Xanthine-Trimethoprim Compositions

Colonies of cockroaches were prepared as described, using the Hawthorne and Las Palms resistant strains.

As shown in Table 8a below, for the Hawthorne strain, feeding was inhibited in relation to the control, in direct ratio to the concentration of trimethoprim in the diet. The maximum decrease of 62% occurred at 4.0% T concentration, which represents a dose of 639 μg of trimethoprim per individual over the first three weeks. Population growth of the Hawthorne strain was controlled at the higher concentrations.

TABLE 8a

Mean individual consumption (ICmg), and percent change (Δ%) in mean population numbers, in colonies of German cockroaches of the Hawthdrne resistant strain offered food without (RC), or with 1% xanthine (RCX), and various concentrations (w/w) of trimethoprim (T %) over time (weeks).

| TIME (wks) | TEST | RC | RCX + T % | | | | |
|---|---|---|---|---|---|---|---|
| | | | 0.5 | 1.0 | 2.0 | 3.0 | 4.0 |
| 3 | ICmg (±SEM) | 42.5 (±0.7) n = 7 | 37.6 (±2.1) n = 3 | 37.1 (±1.7) n = 3 | 30.4 (±2.0) n = 6 | 17.2 (±1.2) n = 6 | 15.9 (±1.4) n = 3 |
| 3 | Δ% | −7% n = 7 | −2% n = 3 | −6% n = 3 | −27% n = 6 | −7S% n = 4 | −79% n = 3 |
| 6 | Δ% | +368% n = 4 | | | −70% n = 3 | −79% n = 4 | −89% n = 3 |
| 9 | Δ% | +606% n = 7 | +369% n = 3 | +298% n = 3 | −17% n = 6 | −95% n = 4 | −94% n = 3 |
| 12 | Δ% | +913% n = 3 | | | −51% n = 3 | −93% n = 3 | −97% n = 3 |

For the Las Palms strain, as shown in Table 8b below, an even decline in ICmg of treated food occurred in direct relation to the increase in concentration of trimethoprim. The maximum inhibition, compared with the control, was 38% at 6% T concentration which constitutes an ingested dose of 1,758 μg of trimethoprim per individual over three weeks. Population numbers were reduced by two-thirds at six weeks of treatment.

TABLE 8b

Mean individual consumption (ICmg) and percent change (Δ%) in mean population number, in colonies of German cockroaches of the Las Palins resistant strain offered food without (RC), or without 1% xanthine (RCX), and with various concentrations (w/w) of trimethoprim (T%) over time (weeks).
n = 3

| TIME (wks) | TEST | RC | RCX + T% | | | |
|---|---|---|---|---|---|---|
| | | | 3.0 | 4.0 | 5.0 | 6.0 |
| 3 | ICmg (±SEM) | 47.0 (±3.8) | 43.0 (±3.5) | 41.3 (±2.2) | 37.0 (±2.3) | 29.3 (±1.8) |
| 3 | Δ% | −12% | −24% | −26% | −43% | −57% |
| 6 | Δ% | +336% | +100% | −37% | −37% | −67% |

EXAMPLE 11

Treatment of Cockroaches with Xanthine-Oxypurinol-Trimethoprim Compositions

Colonies of German cockroaches of the VPI susceptible strain and colonies of the Hawthorne resistant strain were offered either untreated rat chow (RC), or rat chow treated (w/w) with 1% xanthine (RCX), combined with 2% oxypurinol (OXY) and 2% trimethoprim (T). Individual consumption and changes in colony populations results are shown in Tables 9a (VPI strain) and 9b (Hawthorne strain). In both, colonies were virtually extinct by six weeks of treatment, in spite of declines in ICmg of ≧50%.

TABLE 9a

Mean individual consumption (ICmg) and percent change (Δ%) in mean population number in colonies of German cockroaches of the VPI susceptible strain offered food without (RC) or with 1% xanthine (RCX) and with 2% oxypurinol (OXY) and 2% trimethoprim(T) (w/w), over time (weeks).

| TIME (wks) | TEST | RC n = 1 | RCX + 2% OXY + 2% T n = 3 |
|---|---|---|---|
| 3 | ICmg (±SEM) | 71.3 | 34.9 (+1.6) |
| 3 | Δ% | −5% | −68% |
| 6 | Δ% | +955% | −99% |

TABLE 9b

Mean individual consumption (ICmg), and percent change (Δ%) in mean population number in colonies of German cockroaches of the Hawthorne resistant strain offered food with (RC), or with 1% xanthine (RCX) and with 2% oxypurinol (OXY) and 2% trimethoprim (T) (w/w), over time (weeks).

| TIME (wks) | TEST | RC n = 1 | RCX + 2% OXY + 2% T n = 3 |
|---|---|---|---|
| 3 | ICmg (±SEM) | 72 | 34.1 (±0.6) |
| 3 | Δ% | −2.4% | −16% |
| 6 | Δ% | +1416% | −98% |

EXAMPLE 12

Assessment of Purines with Oxypurinol or Trimethoprim

Colonies of cockroaches of the VPI susceptible strain were prepared as previously described. The diets offered were rat chow alone (RC), rat chow (w/w) with it xanthine and 3% trimethoprim (RCX+T), rat chow with it hypoxanthine and 3% trimethoprim (HX+T), rat chow with 1% guanine and 3% trimethoprim (G+T), and rat chow with 1% hypoxanthine and 1% oxypurinol (HX+OXY). Individual consumption (ICmg), and change in population numbers were calculated as before, with the results shown in Table 10, below.

The results, with hypoxanthine and guanine replacing the xanthine component of the diet mixtures, compared closely with those obtained with xanthine. This was the case with both trimethoprim and oxypurinol, with population growth being controlled to extinction of the colonies. Some feeding inhibition occurred in all of the trimethoprim mixtures.

TABLE 10

Mean individual consumption (ICmg), and percent change (Δ%) in mean population numbers, in colonies of German cockroaches of the VPI susceptible strain offered food without (RC), or with 1% of a purine (w/w) and either 3% trimethoprim (T), or 1% oxypurinol (OXY), over time (weeks). Purines were xanthine (X), hypoxanthine (HX), or guanine (G).

| TIME (wks) | TEST | RC n = 2 | RCX + T n = 2 | HX + T n = 2 | G + T n = 2 | HX + OXY n = 1 |
|---|---|---|---|---|---|---|
| 3 | ICmg (±SEM) | 54 (±0) | 26 (±8.0) | 25 (±1.0) | 29 (±8.0) | 42 |
| 3 | Δ% | −5.5 | −68 | −74 | −71 | −17 |
| 6 | Δ% | +152 | −99 | −91 | −94 | −83 |
| 9 | Δ% | +1426 | −100 | −100 | −100 | −100 |

We claim:

1. A composition for controlling an insect pest which salvages, stores, or excretes its nitrogenous wastes via the purine metabolic pathway, comprising a purine selected from the group consisting of xanthine, hypoxanthine, guanine, and mixtures thereof, in an amount of about 1.0%, by weight, and a dihydrofolate reductase inhibitor selected from the group consisting of trimethoprim, methotrexate, and mixtures thereof, in an amount of about 0.1% to about 6.0%, by weight.

2. A composition according to claim 1, wherein the purine is xanthine, in an amount of about 1%, by weight, and the dihydrofolate reductase inhibitor is trimethoprim, in an amount of about 0.1% to about 6.0%, by weight.

3. A composition according to claim 2, wherein the trimethoprim is present in an amount of about 0.1%, by weight.

4. A composition according to claim 2, wherein the trimethoprim is present in an amount of about 0.5%, by weight.

5. A composition according to claim 2, wherein the trimethoprim is present in an amount of about 1.0%, by weight.

6. A composition according to claim 2, wherein the trimethoprim is present in an amount of about 2.0%, by weight.

7. A composition according to claim 2, wherein the trimethoprim is present in an amount of about 3.0%, by weight.

8. A composition according to claim 2, wherein the trimethoprim is present in an amount of about 4.0%, by weight.

9. A composition according to claim 2, wherein the trimethoprim is present in an amount of about 5.0%, by weight.

10. A composition according to claim 2, wherein the trimethoprim is present in an amount of about 6.0%, by weight.

11. A composition according to claim 1, wherein the purine is hypoxanthine, in an amount of about 1.0%, by weight, and the dihydrofolate reductase inhibitor is trimethoprim, in an amount of about 0.1% to about 6.0%, by weight.

12. A composition according to claim 11, wherein the trimethoprim is present in an amount of about 3.0%, by weight.

13. A composition according to claim 1, wherein the purine is guanine, in an amount of about 1.0%, by weight, and the dihydrofolate reductase inhibitor is trimethoprim, an amount of about 0.1% to about 6.0%, by weight.

14. A composition according to claim 13, wherein the trimethoprim is present in an amount of about 3.0%, by weight.

15. A method of controlling an insect pest which salvages, stores, or excretes its nitrogenous wastes via the purine metabolic pathway, which comprises bringing into contact with said pest, a growth-controlling amount of a composition comprising a purine selected from the group consisting of xanthine, hypoxanthine, guanine, and mixtures thereof, in an amount of about 1.0%, by weight, and a dihydrofolate reductase inhibitor selected from the group consisting of trimethoprim, methotrexate, and mixtures thereof, in an amount of about 0.1% to about 6.0%, by weight.

16. A method according to claim 1, wherein the insect is a cockroach.

17. A method according to claim 1, wherein the purine is xanthine, in an amount of about 1.0%, by weight, and the dihydrofolate reductase inhibitor is trimethoprim, in an amount of about 0.1% to about 6.0%, by weight.

18. A method according to claim 17, wherein the trimethoprim is present in an amount of about 0.1%, by weight.

19. A method according to claim 17, wherein the trimethoprim is present in an amount of about 0.5%, by weight.

20. A method according to claim 17, wherein the trimethoprim is present in an amount of about 1.0%, by weight.

21. A method according to claim 17, wherein the trimethoprim is present in an amount of about 2.0%, by weight.

22. A method according to claim 17, wherein the trimethoprim is present in an amount of about 3.0%, by weight.

23. A method according to claim 17, wherein the trimethoprim is present in an amount of about 4.0%, by weight.

24. A method according to claim 17, wherein the trimethoprim is present in an amount of about 5.0%, by weight.

25. A method according to claim 17, wherein the trimethoprim is present in an amount of about 6.0%, by weight.

26. A method according to claim 15, wherein the purine is hypoxanthine, in an amount of about 1.0%, by weight, and the dihydrofolate reductase inhibitor is trimethoprim, in an amount of about 0.1% to about 6.0%, by weight.

27. A method according to claim 26, wherein the trimethoprim is present in an amount of about 3.0%, by weight.

28. A method according to claim 15, wherein the purine is guanine, in an amount of about 1.0%, by weight, and the dihydrofolate reductase inhibitor is trimethoprim, an amount of about 0.1% to about 6.0%, by weight.

29. A method according to claim 28, wherein the trimethoprim is present in an amount of about 3.0%, by weight.

30. The method according to claim 15, wherein said composition is administered by incorporation into a bait or attractant for pest insects which is ingested by said pest insects.

* * * * *